US012322477B1

(12) United States Patent
Hayward (10) Patent No.: US 12,322,477 B1
(45) Date of Patent: *Jun. 3, 2025

(54) METHODS OF EFFICIENTLY TRANSFORMING AND COMPARING RECOMBINABLE DNA INFORMATION

(71) Applicant: John Hayward, Wheaton, IL (US)

(72) Inventor: John Hayward, Wheaton, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/126,039

(22) Filed: Dec. 18, 2020

Related U.S. Application Data

(63) Continuation of application No. 17/112,919, filed on Dec. 4, 2020, now abandoned.

(60) Provisional application No. 62/943,802, filed on Dec. 4, 2019.

(51) Int. Cl.
*G16B 20/00* (2019.01)
*G16B 30/00* (2019.01)
*G16B 50/00* (2019.01)

(52) U.S. Cl.
CPC .............. *G16B 20/00* (2019.02); *G16B 30/00* (2019.02); *G16B 50/00* (2019.02)

(58) Field of Classification Search
CPC ............ C12Q 1/6827; C12Q 2600/156; C12Q 2537/165; C12Q 2539/105; C12Q 1/68; G16B 20/00; G16B 30/00; G16B 40/00; G16B 10/00; G16B 15/00; G16B 20/20; G16B 35/00; G16B 30/10; G16B 50/00; G16B 30/20; G16B 20/10; G16B 25/00; G16B 50/30; G16B 50/50; G16B 25/10; G16B 40/10; G16B 45/00; G16B 50/10; G16B 50/20; G16B 50/40; G16B 5/00; G16B 99/00; G16B 20/40; G16B 5/20; G16B 5/10; G16H 50/20; G16H 50/70; G16H 10/40; G16H 10/60; G16H 50/30; G16H 70/60; C40B 40/06; G06F 16/2365; G06F 16/285; G06F 30/20; G06F 3/048; G06F 7/00; G06F 16/2457; G06F 16/9535; G06F 16/9024; G06F 16/90335; G06F 16/90339; G06F 16/90344; G06F 17/18; G06F 18/22; G06F 18/15; G06F 18/211; G06F 18/2113; G06F 18/29; G06F 18/295; G06F 18/30; H03M 7/3086; H03M 7/70; G06N 5/048; G06N 7/005; G06N 7/01; G05B 19/052

See application file for complete search history.

(56) References Cited

U.S. PATENT DOCUMENTS

| 7,058,515 | B1 * | 6/2006 | Selifonov | .......... | C12N 15/1031 |
| | | | | | 435/91.1 |
| 7,761,238 | B2 * | 7/2010 | Moser | ..................... | G16B 30/00 |
| | | | | | 702/19 |
| 8,428,886 | B2 | 4/2013 | Wong et al. | | |
| 8,463,554 | B2 | 6/2013 | Hon et al. | | |
| 8,645,343 | B2 | 2/2014 | Wong et al. | | |
| 10,036,063 | B2 * | 7/2018 | West | ..................... | C12Q 1/6869 |
| 10,347,361 | B2 | 7/2019 | Adams et al. | | |
| 2007/0127482 | A1 * | 6/2007 | Harris | ....................... | G06F 7/02 |
| | | | | | 370/392 |
| 2010/0057374 | A1 | 3/2010 | Wong et al. | | |
| 2010/0057807 | A1 | 3/2010 | Wong et al. | | |
| 2011/0008775 | A1 * | 1/2011 | Gao | ..................... | C12Q 1/6869 |
| | | | | | 435/6.1 |
| 2013/0338934 | A1 * | 12/2013 | Asadi | ..................... | G16B 30/10 |
| | | | | | 702/20 |
| 2014/0115515 | A1 | 4/2014 | Adams et al. | | |
| 2015/0278435 | A1 * | 10/2015 | Sanborn | ................. | G16B 30/00 |
| | | | | | 702/19 |
| 2016/0306922 | A1 * | 10/2016 | van Rooyen | .......... | G16H 50/20 |
| 2017/0016063 | A1 * | 1/2017 | McGall | ............ | C12Q 2535/122 |
| 2018/0240032 | A1 * | 8/2018 | van Rooyen | .......... | G16B 50/10 |
| 2019/0249229 | A1 * | 8/2019 | Soon-Shiong | ......... | G16H 20/10 |
| 2019/0311784 | A1 | 10/2019 | Adams et al. | | |
| 2020/0042735 | A1 * | 2/2020 | Baluch | ............... | G06F 21/6218 |

FOREIGN PATENT DOCUMENTS

| FR | 2547082 A1 * | 12/1984 |
| JP | H08505483 * | 6/1996 |
| WO | 2010024894 | 3/2010 |

(Continued)

OTHER PUBLICATIONS

Yihui, L. A sequential iterative refinement optimization method to multiple sequence alignment. (2004) National University of Singapore. 127 pages. (Year: 2004).*
Zhang, J. Transforming and optimizing irregular applications for parallel architectures (2017) Virginia polytechnic institute and state university. 265 pages. (Year: 2017).*
Yano, M. CLAST: CUDA implemented large scale alignment search tool. BMC bioinformatics (2014) 15:406, 13 pages. (Year: 2014).*
Turakhia, Y. Darwin: a hardware acceleration framework for genomic sequence alignment. (2017) biorXiv. 15 pages. doi.org/10.1101/092171. (Year: 2017).*
Shaji (2016) fast genotyping of known SNP through approximate k-mer matching. Bioinformatics 32:i538-i544. (Year: 2016).*

(Continued)

*Primary Examiner* — Mary K Zeman
(74) *Attorney, Agent, or Firm* — Sierra IP Law, PC; William K. Nelson (57) ABSTRACT

The present invention relates to an improved system and method for analyze data from submitted DNA kit and/or genome data form database records so as to compare sequences for determining the level of SNP homology between the two tested sequences. The DNA calling data is compared in a stepwise block by block manner, where the blocks for the compared sequences have data blocks in bit-word lengths of the processor performing the sequence comparison analysis. The blocks are compared in block sets having a minimum cM length, where the block comparisons are initiated at the last block of the minimum length block sets and proceed in a retrograde manner.

11 Claims, 4 Drawing Sheets

(56) References Cited

FOREIGN PATENT DOCUMENTS

WO      2014066635      5/2014

OTHER PUBLICATIONS

Ranwez, V. MACSE: multiple alignment of coding sequences accounting for frameshifts and stop codons. (2011) vol. 6 Issue 9 e22594. 10 pages. (Year: 2011).*
Pockrandt, C. EPR-dictionaries: a practical and fast data structure for constant time searches in unidirectional and bidirectional FM indices. In RECOMB 2017, LNBI 10229, Sahinalp (ed) pp. 190-206, Springer International Publishing. (Year: 2017).*
Liu, P. (2017) 3D-stacked many-core architecture for biological sequence analysis problems. Int J Parallel Prog. vol. 45: 1420-1460. (Year: 2017).*
Lanjanian, H. (2019) Block alignment: new representation and comparison method to study genomes. vol. 111, p. 1590-1603. (Year: 2019).*
Gupta, S. (2019) RAPID: a ReRAM processing in-Memory architecture for DNA sequence alignment. IEEE 6 pages. (Year: 2019).*
Sandes, E.F.O. (2016) IEEE transactions on parallel and distributed systems. vol. 27 No 10. pp. 2838-2850. (Year: 2016).*
Yin (2017) Computing platforms for Bio Biological Analytics: Perspectives and Challenges. Computational and Structural Biotechnology Journal 15:402-411 (Year: 2017).*
Alser (2017) Gatekeeper: a new hardware architecture for accelerating pre-alignment in DNA short read mapping. Bioinformatics 33(21) 3355-3363. (Year: 2017).*
Tran, T.T. et al. (2014) Bit-parallel approximate pattern matching on the Xeon Phi Coprocessor. IEEE 26th Int. Symposium on Computer Architecture and high performance computing. p. 81-89. (Year: 2014).*
Konagurthu, A. S. et al. (2010) Design of an efficient out of core read alignment algorithm. WABI, LNBI 6293 p. 189-201. (Year: 2010).*
Durbin, R. (2014) efficient haplotype matching and storage using the positional Burrows-Wheeler transform (PWBT). Bioinformatics 30:9 1266-1272. (Year: 2014).*
Wu, T.D. et al. 2016 Chapter 15: GMAP and GSNAP for genomic sequence alignment: enhancements to speed accuracy and functionality. Mathe and Davis (eds) Statistical genomics: Methods and protocols, Methods in molecular biology vol. 1418, p. 283-334. (Year: 2016).*
GATK website information about VCF file formats. Downloaded Dec. 13, 2022. (Year: 2022).*
PLINK 1.9 website formats downloaded Dec. 13, 2022 cog-genomics. org. (Year: 2022).*
UCSC website listing data file formats, downloaded Dec. 13, 2022, genome.ucsc.edu. (Year: 2022).*
GWASTools Gogarten, Nov. 2022, Data Formats in GWASTools. (Year: 2022).*
Complete genomics manual 2013, sequence services pipelines. (Year: 2013).*
NIH NHGRI definition of centimorgan. downloaded Dec. 13, 2022 (Year: 2022).*
Mula et al (2017) Faster population counts using AVX2 instructions. The British Computer Society, vol. 61, No. 1 advance access publication May 24, 2017, 10 pages. (Year: 2017).*
Wikipedia definition of Boolean algebra, downloaded Jul. 21, 2023 (Year: 2023).*
Zheng, X. (2017) SeqArray—a storage-efficient high-performance data format for WGS variant calls. Bioinformatics 33(15) 2251-2257 and supplemental material. (Year: 2017).*
Zheng, X. (2015) A tutorial for the R/ Bioconductor package SNPRelate. Downloaded from Bioconductor (dot) com, Jul. 18, 2023. 27 pages. (Year: 2015).*
Chang (2015) Second-generation PLINK: rising to the challenge of larger and richer datasets. Gigascience vol. 4:7, 16 pages and supplemental material. (Year: 2015).*
Layer et al. (2016) Efficient genotype compression and analysis of large genetic variation data sets. Nature Methods, 11:1 p. 63-68, with integrated supplemental information, and additional supplemental figures. (Year: 2016).*
GENESIS package manual, Oct. 16, 2018, downloaded from Bioconductor Jul. 18, 2023. 51 pages. (Year: 2018).*
SeqArray package manual, Jul. 15, 2023, downloaded from Bioconductor Jul. 18, 2023. 79 pages. (Year: 2023).*
SNPRelate package manual, Jul. 17, 2023, downloaded from Bioconductor Jul. 18, 2023, 108 pages. (Year: 2023).*
Daily, J. (2016) Parasail: SIMD C library for global, semi-global and local pairwise sequence alignments. BMC Bioinformatics 17:81, 11 pages. (Year: 2016).*

\* cited by examiner

| Template 2010 | Data Blocks 2023A | Data Blocks 2023B | Data Blocks 2023C |
|---|---|---|---|
| SNP Locus 1 | 1 | 0 (A-T) | 1 |
| SNP Locus 2 | 1 | 1 (C-G) | 1 |
| *SNP Loci 3-63 omitted for convenience* | | | |
| SNP Locus 64 | 1 | 1 (C-G) | 1 |
| SNP Locus 65 | 1 | 0 (A-T) | 1 |
| *SNP Loci 66-127 omitted for convenience* | | | |
| SNP Locus 128 | 1 | 1 (C-G) | 1 |
| SNP Locus 129 | 0 | n/a | 0 |
| *SNP Loci 130-191 omitted for convenience* | | | |
| SNP Locus 192 | 0 | n/a | 1 |
| *Additional blocks omitted for convenience* | | | |

1st 64-bit block
2nd 64-bit block
3rd 64-bit block

METHODS OF EFFICIENTLY TRANSFORMING AND COMPARING RECOMBINABLE DNA INFORMATION

FIELD OF THE INVENTION

The present invention relates to a method, an apparatus, a computer program embodied on a computer readable storage medium, and a processor, such as a processor (e.g., one or more devices, circuits, and/or processing cores configured to process data, such as computer program instructions) operable to execute instructions stored on and/or provided by a memory in electronic communication with the processor for converting recombinable DNA information from a DNA analysis kit into computer data in an efficient form for comparison to another data set.

DISCUSSION OF THE BACKGROUND

The genetic material of animals is found in deoxyribonucleic acid, which includes a double-stranded helix bound together at complementary base pairs. The base pairs consist of the nucleotides adenine (A), thymine (T), guanine (G) and cytosine (C), which pair together in complementary base pairs across the double helix. Adenine only pairs with thymine and vice versa (forming A-T base pairs), and cytosine only pairs with guanine and vice versa (forming C-G base pairs). The sequence of these base pairs are organized into genes, which encode the polypeptides (and thus the proteins) that can be built by the cells of the organism. Essentially the genes comprised on the DNA provide the blue print for the biochemistry of the cells of the organism.

Generally speaking, each person has 22 autosomal (non-sex) chromosomes and two sex chromosomes (a female has two X chromosomes, and a male has an X chromosome and a Y chromosome). The chromosome are highly organized, individually packaged stretches of DNA that each include distinct sets of genes. The complete DNA instruction book, or genome, for a human contains about 3 billion base pairs of these nucleotides, each base pair being located at a locus on a particular chromosome. Autosomal chromosomes and X chromosomes can recombine (through cross-over events) and independently assort through the process of meiosis. Meiosis is the cell-division process carried out in the gonads of an individual that create gametes (sperm or egg). During this process the chromosomes of the individual may be shuffled to a limited extent in the production of gametes prior to fertilization: combining of the individual's gamete (e.g., sperm) with the compatible gamete of another (e.g., an egg or ovum).

The recombination of chromosomes in each parent contributes to the genetic variability in a manner that can be analyzed to determine relatedness of individuals. The offspring receives a copy of each chromosome from each parent, and the copies of each gene on those chromosomes will vary depending on the recombination due to crossover events. In crossover events, one copy of a chromosome (e.g., the paternal copy of the chromosome) crosses over with the other copy (e.g., the maternal copy of the chromosome) during meiosis and the crossed-over portions of the chromosomes are swapped, such that each resulting chromosome is a mix between paternal and maternal DNA. If this individual (e.g., a male) then produces offspring from a gamete that contains the crossed-over (mixed) chromosome of the parent (i.e., a mixture of the paternal grandmother and grandfather chromosomes), the child will have the mixed chromosome in each of his or her cells. However, the position and sequence of the genes on the chromosomes are maintained even with the recombination, which only effects the version of the genes that the offspring receives from the parent.

Such shuffling accumulates across generations creating greater variations with hereditary distance, and as a result only proximate familial relatives share long stretches of genomic regions where their recombinable DNA is largely the same. Such regions are referred to as "Identical by Descent" (IBD) regions because they arose from the same DNA sequences in an earlier generation. DNA sequencing and genealogical analysis vendors such as Ancestry, 23andMe and Family Tree DNA utilize this property of recombinable DNA to provide genetic and genealogical analysis of their customer's genome, indicating likely geographic and ethnic origins and family tree analysis.

The analysis may include the steps of sequencing the entire genome of the customer and comparing it to the genomes of other customers and/or to a database of genomes. The comparison may be made by identifying DNA markers that tend to vary in different individuals and tend to vary more with greater genealogical distance. Such markers include Single Nucleotide Polymorphisms (SNPs), which are points along the genome with two or more common variations. The variability of base pairs at SNPs has a predictable probability, but the probability varies at different SNP loci across the autosomal DNA. The number of base pairs over which there is an expected 1 percent probability that a crossover event will occur between two positions within a chromosome is defined as 1 centimorgan (cM) or 1 map unit. Across all chromosomes there are on average about 33.8 crossovers so the genetic distance across all chromosomes is about 3400 cM. The closeness of the genealogical relationship between two individuals may be determined by comparing the base pairs present at different SNP locations in the two individuals' respective genomes, which indirectly indicates the segments of DNA between the genomes that match.

The genealogical analysis companies may use a method called half-matching to compare the SNPs in the genome of a customer to other genomes. Half matching involves comparing the DNA samples from two individuals to look for mismatches between the samples at specific SNPs across both copies of individuals' the chromosomes. The two DNA samples are examined for matching at each (or a predetermined number of) known SNP loci in the human genome. If there is a match between at least one of the chromosomes for one individual with one of the chromosomes of the other individual, the half-matching criterion is met. If there is no half-matching between the two individuals' DNA at a particular locus, there is a mismatch. For a comparison between parent (e.g., father) and child, there will be no mismatches, since the child has inherited one base pair at each locus from the parent. The total shared cM would be close to 3400 cM, which is equivalent to the entire length of a person's autosomal DNA (all of the 22 autosomal chromosome). As relations are further removed, mismatches become more prevalent.

The genealogical distance between two individuals follows a predictable pattern that reliably correlates with how closely related the individuals happen to be. For example, two siblings will share about 25% fully matching SNP loci and about 50% half matching SNP loci, yielding about 75% SNPs that at least half-match. The ranges of cM for 99% of siblings are about 2,209 cM to about 3,384 cM (identical twins). The mismatching SNPs due to crossover are somewhat random when comparing non-identical siblings. If we consider grandparents and cousins, a person will share about 50% half matching loci with each grandparent and about 25% half matching loci with a first cousin. As you consider more distant relations, the average percentage goes down. For example, a person shares about 3.125% half and fully matching loci with second cousins once removed, which would correspond to 106 cM. However, it is to be understood that there is significant variation in the extent of matching between such distant relations, with the largest matching segments between such relations ranging from 0 cM to 316 cM with average 123 cM.

The conventional genomic analysis performed by genealogical analysis vendors (e.g., 23andMe, Ancestry, etc.) is to serially compare each SNP location in a submitted DNA kit with each pre-existing genome sequence stored in the vendors database in order to identify any close matches. A sufficiently close match between the submitted DNA kit and a genome sequence in the database indicates some level of familial relationship (e.g., second cousins, etc.). The number of SNP locations vary based on the particular DNA microarray technology (chip) that the vendor utilizes, but the number of SNPs analyzed per comparison generally falls in the range of 600,000 to 900,000 SNPs. Stepwise analysis of such a large number of data points for many inter-genome comparisons (comparisons between the submitted DNA kit and each genome sequence in the database) is onerous, requiring a very large number of computations. Such analysis may be done by computer after the SNPs data is converted into a data file. However, the sheer number of comparisons results in an enormous computational load.

Therefore, there is need for improved and more efficient computing methods for analyzing genomes for genealogical mapping and other purposes.

SUMMARY OF THE INVENTION

The present invention provides an improved data conversion and analysis technique for genetic comparisons between individual genomes that significantly improves the computing efficiency of the comparisons.

The present invention converts DNA chip (microarray technology) data provided by a DNA collection kit into a data file format that can be efficiently used in current computing systems (e.g., 32-bit, 64-bit, 128-bit, etc.) through a novel analysis process. First, the data from the DNA chip may be organized according to a comprehensive SNPs template of all known SNPs that have a sufficiently level of variability across individuals that they can be used to analyze two genomes for relatedness. In some embodiments, this template may include about 1.4 million SNPs in sequential genomic order (e.g., from human autosomal chromosome 1 to autosomal chromosome 22). However, the number of SNPs in the template may be varied depending on the chromosomes selected for analysis (e.g., the X chromosome may be included in the analysis, certain chromosomes may be excluded from the analysis, etc.). The number of SNPs in the SNPs template may be determined by (1) selecting the chromosomes to be analyzed, and (2) applying a frequency filter to known SNPs in the human genome to determine which SNPs vary often enough between individuals to warrant consideration in a half-matching analysis. The applied frequency of variance between individuals may be selected based on the statistical reliability desired, the desired computing efficiency of DNA comparison analysis, and other criteria. Applying a reasonable threshold for frequency of variability to the entire human genome for the SNPs yields about 1.4 million SNPs for analysis. The SNPs that are pre-selected for analysis are used to build an analysis template identifying those SNPs that qualify for analysis that can be used to select and package SNP data from DNA collection kits to be analyzed.

The SNPs template may include all SNPs that are analyzed by genealogical analysis vendors. While the selection of SNPs varies from one vendor to the next based on the DNA chip technology they employ and the particular criteria they apply, the predominant proportions of the SNPs analyzed by various vendors overlap and allow for comparison analysis of DNA kit data from various vendors using the SNP template. The DNA genome data from a vendor's DNA kit can be adapted to correspond to the SNPs template so that comparison analysis with genomic data for another individual acquired from a different vendor can be compared without the need for sequence alignment analysis between the two genomes. All of the SNP data for each genome is prepackaged into a data file that matches the SNP template. The configuration of the SNP data from DNA kit into the SNP template format pre-aligns the data into a standardized arrangement of the selected SNPs (e.g., the roughly 1.4 million known SNPs of sufficient variability) into blocks equal to the bit-word length of the processor (e.g., a microprocessor) used to compare with SNP data from another individual's DNA kit.

The DNA kit data provided from a particular DNA chip may be analyzed and the SNP data therefrom may be converted into digital data in blocks of pre-determined bit lengths that correspond to the word length of a processing system (e.g., 32 bit, 64 bit, 128 bit, etc.). In some implementations, an individual's DNA genome data may be acquired from one or more databases and may be organized into digital data blocks as disclosed herein. The number of bits in each block may be the same as the word length of the processor to allow the block to be analyzed in one computing operation to achieve greater processing efficiency. In some embodiments, the blocks each have 64 bits, such that they can be analyzed by current 64-bit processing systems. However, it should be noted that the methods described herein can be adapted to other word-length processing, such as 32 bit, 128 bit, etc.

The DNA kit or other DNA genome data may be organized into a data file having two or more sets of blocks that correspond to each position in the SNPs template, with the first block indicating whether or not a particular SNP was analyzed and found to be homozygous, providing useful data for a half-matching analysis. Half-matching analysis involves a bitwise operation may be performed on the data file of a customer in comparison with another data file for another individual's genome (the "comparable"), wherein each compared bit in each data file represents a designated value for a particular base pair at an SNP location. Only SNP locations that are homozygous at an SNP base pair are analyzed in order to simplify the analysis to a single bit analysis at each homozygous SNP location—the half-matching scheme. Heterozygous base pairs a particular SNP locus are not useful because they cannot be effectively analyzed in a bit to bit comparison between two genomes. A heterozygous condition at a locus has two different base pairs, and thus the identity of the base pairs cannot be encoded in a single bit. In contrast, a homozygous set of base pairs at a locus can be encoded by a single bit (e.g., "0" can represent homozygous A-T base pairs, and "1" can represent homozygous C-G base pairs), and is thus useful for a bitwise analysis of SNP loci in the analyzed genome.

Applying the bit-wise half-matching process, a user with no opposite-homozygous calls between a beginning locus and an ending locus of a segment of DNA may be deemed as an IBD region for the customer and the comparable, if the DNA segment is of sufficient length to satisfy a chosen statistical standard. In contrast, if the customer has one or more opposite-homozygotes from the comparable, the customer is deemed not to share IBD with the comparable in the analyzed DNA segment. The comparison process may be carried out for the customer between multiple comparable genomes to analyze the genealogical relationship between the customer and various comparable genomes in a database. Carrying out this computation process for hundreds of thousands of SNPs multiple times (e.g., for each genome stored in a database of many thousands or even millions of genomes) is highly time and resource consuming. For example, a newly submitted genome (e.g., from a new DNA analysis kit) is "batch processed", which involves comparing the newly submitted genome to all or nearly existing genomes in a database. This is done because this DNA comparison analysis is usually performed for the purpose of identifying potential familial relations in the database and to identify gene sequences that are characteristic of a particular ethnic or national origin. Thus, the utility of the DNA comparison analysis largely derives from the comprehensive batch processing operation.

The genome to be analyzed must be appropriately organized to take advantage of the homozygous SNP base pairs in the half-matching analysis. Each locus in the genome (including all SNP locations) have two base pairs (the base pair on each of the corresponding chromosomes from individual's parents). There are only two possible base pairs at each locus (A-T and C-G). Thus, if a person is heterozygous, both possible base pairs are present in the genome and there will be a half-match between the individual and the compared genome, regardless of the genotype of the compared genome at that particular locus. Thus, the SNPs compared between two genomes may be limited to SNP loci for which the particular individual has a homozygous genotype. The data captured in the first block provides an indicator as to whether the SNPs are appropriate for analysis (e.g., a "1" for the presence of homozygous base pairs at a SNP location, and a "0" value for no data or heterozygous base pairs). Thus, each SNP locus has a corresponding 1-bit datum in the first set of data blocks, referred to herein as a "token", indicating whether the DNA kit or database record indicated a homozygous pairing for the individual at the SNP locus. If the SNP data for a particular position in the SNPs template indicates heterozygosity or was not provided in the data from the DNA kit or database record, the token at such position would indicate the absence of a homozygous base pairs.

The second set of data block may include a token at each SNP locus that indicates the identity of the homozygous base pairs at the SNP locus. The second block provides the single bit identification (token) of the homozygous base pairs, e.g., where one base pair (e.g., A-T) is represented by a "0" value and the other possible base pair (e.g., C-G) is represented by a "1", enabling a single computing operation for each block. A simple machine analysis can be conducted between the compared blocks of the two kits to determine whether the kits match or mismatch at the loci analyzed in the compared blocks in one computing operation. A bitwise OR operation is performed to generate a result array for the DNA kit or genome data (the "test kit") being compared to a second genome data set from a database or other kit (the "comparison data"). For example, in a processor having a 64-bit word length, a 64-bit block representing 64 SNP loci from the string of second blocks for the test kit is compared with a 64-bit block representing the same 64 SNP loci from the comparison data's string of second blocks through a OR single operation of the 64-bit processor. The OR operation may include OR analysis between each set of matching tokens (matching loci) in each of the 64-bit blocks: e.g., OR operation between the $1^{st}$ bit of the test kit block with the $1^{st}$ bit of the comparison kit block, OR operation between the $2^{nd}$ bit of the test kit block with the $2^{nd}$ bit of the comparison kit block, and so on. If no opposite-homozygous tokens between corresponding tokens (matching loci) in the two 64-bit blocks are present, all OR operation values will be zero, resulting in a total OR operation value of 0 in the array for the compared bit-word length blocks. In the case of no mismatches, the analysis continues to the next block. It should be noted that the first block analysis of the test kit restricts the reporting of the second block analysis to only SNP loci where the genotype of the test kit is homozygous, thereby providing a filter on the second block analysis, identifying only the loci that are (1) relevant to the half-matching analysis and (2) reportable in the comparison analysis.

In some embodiments, the data file for the genome may have a 3-bits per position in the SNP template, and thus has a third token for each SNP locus. In such embodiments, the first block may include a one-bit token at each locus that indicates whether the SNP was analyzed by the DNA kit and is homozygous, the second block may include a one-bit token at each locus that identifies the homozygous base pairs at the SNP locus, and the third block may include a one-bit token at each locus that indicates whether a heterozygous SNP is present at the locus. The third block token may indicate a heterozygous base pair at a locus simply by indicating whether there was data collected for the locus in the initial DNA collection kit analysis (e.g., a "1" for presence of base pair data at the locus and "0" for no data), and then comparing the third block data to the first block data for the tested sequence (e.g., through an OR operation) to indicate whether the first block indicated absence of a homozygous base pair at the locus (e.g., "0" bit) and the third block indicates the presence of data at the locus (e.g., a "1" bit)—see, e.g., SNP locus 192 in FIG. 3. This comparison of the first block and third block data for the same sequence (e.g., the test genome) would indicate whether heterozygous base pairs are present in the test genome. Thus, the first two bits are the same as they are for the 2-bit implementation, and the third bit provides additional information about whether a SNP was tested at a locus and was found to be heterozygous. The 3-bit version allows for exact reporting on the number of SNPs in a matching segment and the overlap of reported SNPs between two compared kits, rather than estimates of these numbers. In general, about 30% of SNPs are heterozygous in a genome, and thus the half-matching scheme omits a large amount of data points from the analysis. The analysis of heterozygous matching allows for better analysis of kits from different DNA microarray chips with significant differences in the reported SNPs (referred to as "poor alignment"). If the number of overlapping SNPs is too small, the kits may not be reliably analyzed. In the 2-bit version, fewer of the overlapping SNPs are available for analysis because only SNPs for which the kit is homozygous are analyzed, and thus kits that may have a sufficient number of overlapping SNPs may not be analyzed under the half-matching scheme because only the homozygous SNPs are considered. However, the 3-bit analysis allows for examination of the heterozygous overlapping SNPs and thus an exact counting of the number of overlapping SNPs. With the analysis of the 3rd bit, two kits may have a sufficient number of overlaps for reliable half-matching analysis.

The 3-bit version also helps with analyzing and satisfying a minimum SNP parameter for a "matching" segment. In addition to the minimum cM segment length requirement, the matching criteria may include a minimum number of SNPs parameter (e.g., a minimum of 400 SNPs) to qualify a matching segment as having a sufficient length to be statistically meaningful. The 3-bit version can account for both for reported homozygous and heterozygous SNPs in the segment, thus improving the reliability of the increasing the reported total SNPs and making it more likely that a segment having a sufficient number of SNPs is reported as such.

The block packaging of the DNA kit data is a novel approach for analyzing the base pair data that avoids having to sequentially analyze all of the SNPs loci in the genomic data. The presently disclosed methods include a machine executable instruction performed by one or more processors (e.g., microprocessors) that analyzes the blocks within a segment of SNP loci of a pre-determined length in a retrograde manner that allows for many of the blocks in the genomic data file to be skipped over without sacrificing any useful information while reducing the computing load of the genomic comparison between two individuals, an individual and other genomic data set (e.g., another species, an idealized genomic data set, etc.), or other genomic comparisons. The machine executable instructions may first determine the required minimum CM length criteria of a DNA segment: a predetermined length of a matching DNA segment needed to be statistically acceptable IBD match, e.g., 7 cM. The predetermined minimum cM length criteria may be chosen by the user based on the desired statistical reliability of the genomic half-matching analysis. Based on the required cM length criteria of a segment, the processor(s) may precompute how many consecutive blocks need to be free of SNP mismatches to satisfy the minimum CM length criteria. The machine executable instructions may then direct the processor(s) to find the last block in the pre-determined segment length and begin comparing the blocks in the segment in a retrograde direction. This is done because in the vast majority of instances, a mismatch will occur after 1 or 2 blocks if the compared segments between the genomes do not match. Once a mismatch is found in the segment, every other block in the segment is ignored and the processor(s) advances to the next segment without using computing bandwidth or time examining the remaining blocks in the segment, which will usually constitute most of the blocks therein. The next segment for analysis may begin at the first mismatch encountered in the retrograde analysis of the blocks in the previous segment and may end at a consecutive number of blocks that corresponds to the minimum cM length criteria. The machine executable instructions may then direct the processor(s) to start the retrograde analysis process again at the last block in the second segment.

In the event that a segment represented by a consecutive set of blocks that satisfies the minimum CM length is free of mismatches, it may be counted as an IBD match (i.e., it has been determined to have a number of consecutive blocks without mismatches that is at least as long as the minimum CM length and is ended by a block with at least one mismatch). In other implementations, the segment may be examined in more detail. For example, the blocks of the segment can be processed to determine the last mismatch position in the first block and the first mismatch position in last block. From there, a more precise calculation of the total length of the matching segment can be determined. This may be particularly important where the segment just meets the minimum CM length requirement. Because of the nature of the analysis of each 64-bit block (it being analyzed in one computing operation, giving a single output), there are situations where a segment length is determined to be about equal to the minimum segment cM length based on the block analysis, and thus further analysis may be needed in order to determine that the segment actually meets the minimum CM length. For example, if there are 64 SNPs represented in each block, and if a mismatch is found in a block, it may be near the beginning of the 64 bits or near the end. After the mismatch ("mismatch 1") is found, the block analysis will proceed from the block containing the mismatch 1 to determine whether there is a segment beyond mismatch 1 that has sufficient number of matching blocks to satisfy the minimum cM length. If the segment length meets only the minimum number of blocks when a second mismatch ("mismatch 2") is found, it is indeterminate whether the segment actually meets the minimum CM length because mismatch 1 may be near the end of the 64 bits in the first block and mismatch 2 may be near the beginning of the 64 bits in the last block. This would render the segment between mismatch 1 and mismatch 2 slightly less than the minimum CM length. The exact length of the segment can be determined by further processing, such as by determining the locus of the SNP mismatches 1 and 2 within the beginning and end blocks of the segment and calculating the distance between them. In other implementations, the minimum number of blocks needed to meet the cM length may be adjusted to include one additional block to account for such eventualities.

As mentioned above, the processor may evaluate the overlapping homozygous SNPs (in the 2-bit version), and optionally the total number of overlapping SNPs present (in the 3-bit version) in the segment. These analyses can be done quickly because there are simple machine instructions to count the number of bits in a block that include a bit indicating the presence of a SNP in a block (e.g., a 1 for presence vs. a 0 for absence). The processor may further analyze overlapping SNPs to check for GAP distance and apply a sum of values associated with each SNP position, such as by Q calculations. Q calculations are an advanced statistical method that puts a value on each position based on the probability that two kits will match by chance at this position. These operations on individual SNPs can take place fairly quickly since there are machine instructions to advance to the next bit in a block compared to the method used in conventional methods.

The apparatus of the present invention may include several software tools for executing the steps of the process described herein. These tools may include the following:

a. A software module or tool having machine-readable instructions operable to direct a processor to convert the data from a DNA kit into a data file having 2 or 3 sets of blocks that include a pre-determined number of positions that correspond to the SNPs template, where the blocks are each equal in bit length to the bit-word length of the processor(s) of the electronic analysis system.
 b. A software module or tool having machine-readable instructions operable to direct a processor to calculate the cM length between positions in the SNPs template.
 c. A software module or tool having machine-readable instructions operable to direct a processor to precompute the minimum cM segment length and convert that into a number of consecutive blocks needed to meet the minimum cM length.

d. A software module or tool having machine-readable instructions operable to direct processor(s) to compare the data of the blocks of two comparable sets of blocks from two DNA kits for mismatches in a retrograde scheme starting from a distal end of a block segment of predetermined length, and then advancing the matching analysis to a new segment when a mismatch is found, where the new segment may start at the mismatch.

It is an objective of the present invention to provide a genetic analysis process and system operable to reduce the time and computing power it takes to identify reportable homologous segments during genetic comparison analysis of two DNA kits, and to reduce the digital processing required to store DNA kit data files.

It is a further objective of the present invention to provide a genetic analysis process and system operable to utilize a template sequentially covering all known SNPs that have sufficiently frequent variability to be useful for DNA comparison for genealogical analysis.

It is a further objective of the present invention to provide a genetic analysis process and system operable to perform genealogical comparison analysis between two DNA data sets provided by different vendors utilizing different DNA chip technologies, without the need to perform alignment analyses and calculations to coordinate the SNP data from DNA kits, and other genome data sources.

It is a further objective of the present invention to provide a genetic analysis process and system operable to package data from various DNA chip technologies into data blocks that having a number of bits that match the word length of the computing system being used for the analysis (e.g., 64 bit) and that contain data for (1) presence or absence of each SNP captured by the DNA chip and (2) the half-match identity of the base pair. The blocks may be designed to correspond to the positions in the template, such that each kit can be compared block by block, regardless of the vendor from which the kit was received.

It is a further objective of the present invention to provide a genetic analysis process and system operable to analyze for the presence of heterozygous SNPs so that the exact total of SNPs and exact overlap determinations between DNA kits can be made.

It is a further objective of the present invention to provide a genetic analysis process and system operable to analyze each data block in one computing operation using simple machine instructions. For example, a block indicating presence of a SNP (where 1 indicates presence and 0 indicates absence for each bit), if the block returns any 1 value, the block will be analyzed for half-match identities of the base pairs represented in the block. Also, if there are no SNPs present in the block, the processor may skip all analysis of the half-match identities of the SNPs in that block.

DETAILED DESCRIPTION OF THE EMBODIMENTS

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

The present invention can be implemented in numerous ways, including as a process; an apparatus; a system; a composition of matter; a computer program product embodied on a computer readable storage medium; and/or one or more processor(s), such as processor(s) operable to execute instructions stored on and/or provided by a memory coupled to the processor. In this specification, these implementations, or any other form that the invention may take, may be referred to as methods, techniques, and electronic systems. A component such as a processor or a memory described as being operable to perform a task may be implemented as a general component that is temporarily configured or operable to perform the task at a given time or a specific component that is manufactured to perform the task. As used herein, the term "processor" refers to one or more devices, circuits, and/or processing cores configured to process data, such as machine executable computer program instructions.

Figure 1:
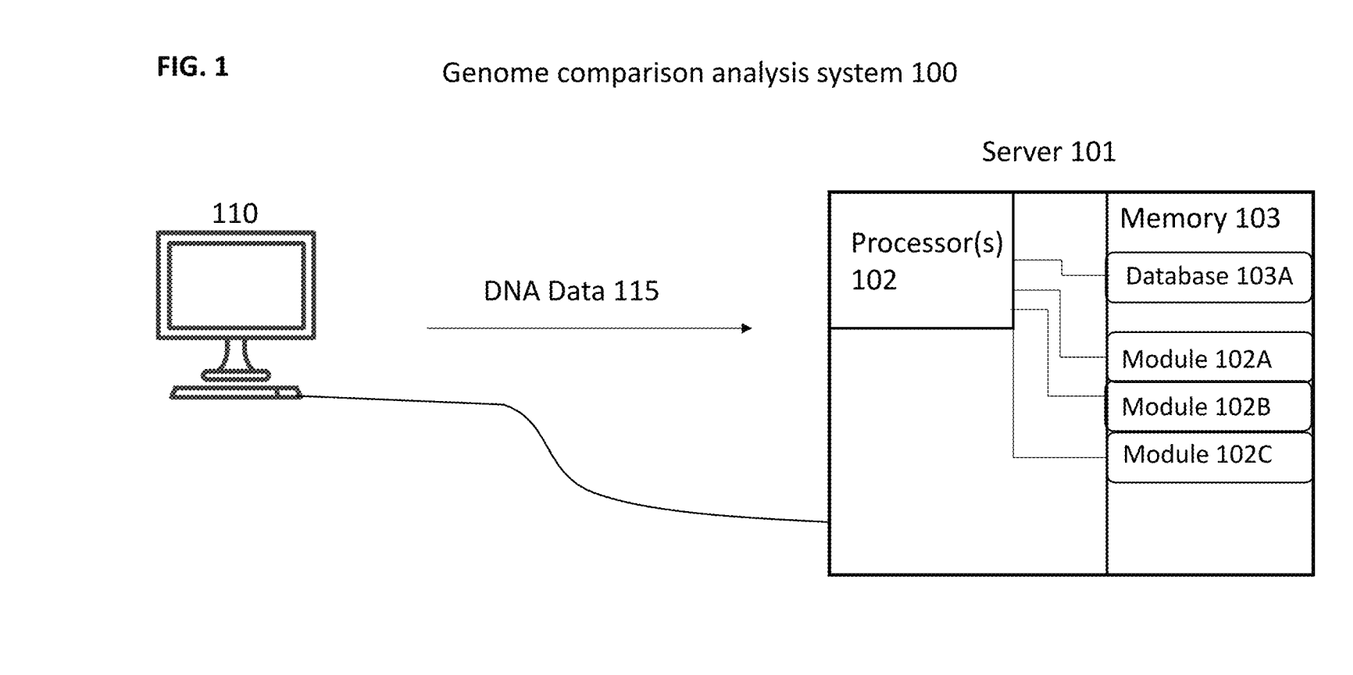
FIG. 1 shows an electronic genome analysis system according to an embodiment of the present invention.

FIG. 1 shows a block diagram of a system 100 operable to analyze the genotype calling data collected from an individual sample. The system through a first client computer or terminal 110 operatively connected (e.g., by wired or wireless electronic communication) to a local or network accessible server 101 having one or more processors 102. The client 110 may have access to and provides sequence data from a database 103A stored in a memory 103. Typically, the database 103A may include a plurality of genetic sequences obtained for example by sequencing one or more biological test samples. The sequence database 103A a shared database connected with a server 102 to which a user controls access. The server 101 and/or client 110 may include several software tools for analyzing the sample calling data in comparison to one or more pre-selected sequences from the database 103A.

A software module 102A (machine executable instructions) may be operable to direct processor(s) 102 to convert the data from the individual sample (e.g., a DNA kit) into a data file having 2 or 3 sets of data blocks that include a pre-determined number of positions that correspond to a pre-defined SNPs template, where the number of bits stored in the blocks correspond to the processor bit integer architecture of the system (e.g., 32 bit, 64 bit, 128 bit, etc.). That is, the number of bits in a data block may be equal to the bit-word length of a computer processor, such that the data block may be analyzed in a single computation operation by the computer processor. The software modules 102A, 102B, 102C, and other software utilized in the system 100 may be stored in the memory 103 of the server 101, which may be in electronic communication with and accessible to processor(s) 102.

The DNA data 115 of the test sample may be data from a human DNA sample acquired using a DNA sequencing kit. The DNA sample may be provided by an individual via a sample of saliva on a swab. The sample may be analyzed using a genotyping platform, which is a set of Single Nucleotide Polymorphisms (SNPs) and a method for assaying the allele values for those SNPs. This process is known as hybridization and yields different hybridization intensity values for each locus. Genotype values may be assigned to the base pairs of each SNP by comparing the relative strength of these intensities. Assigning these values to the individual's SNPs is referred to as "calling" or "genotype calling". Examples of different genotyping platforms include the Illumina HumanHap550v3 genotyping chip or full sequencing using ABI SOLiD. The genotype calling data may be subsequently used to analyze the genetic sequence of the individual by comparison to other genetic sequences stored in a database. The DNA data 115 may be provided to the server 101 via electronic transfer from the client 110 or obtained from another source. The received DNA data 115 may be stored in memory 103 once received.

The test sample data 115 may be processed according to the pre-defined template for organizing the individual sample data into a standardized, analyzable format. The processor(s) 102 may also execute software module 102B (machine executable instructions) operable to calculate the cM length between the positions of the SNPs in the pre-defined template, and to precompute the minimum cM segment length for determining relatedness of two samples (this may be a preselected value corresponding to a particular application, e.g., 7 cM), and convert that into a pre-defined number of consecutive blocks needed to meet the minimum CM length.

The processor(s) analyze data from submitted kit data and/or genome data from the database 103A so as to compare a test sequence with one or more reference sequences, such as a consensus sequence or one or more pre-selected sequences of interest from the database 103A (e.g., the sequence of a person related to the person from which the sample is obtained, or batch processing operation in which the test sequence is compared to all genomes in the database 103A).

The test sample (other genome data files may be analyzed) and a reference sequence may be analyzed by the processor(s) 102 with a plurality of filters or algorithms to identify half-matching SNP cites between the sample sequence and the one or more reference sequences. A software module 102C (machine executable instructions) may provide instructions that enable processor(s) 102 to compare the data of the blocks of two aligned comparable sets of blocks from the sample and one or more pre-selected reference samples for mismatches in a retrograde scheme starting from a distal end of a block segment of predetermined length, and then advancing the matching analysis to a new segment when a mismatch is found, where the new segment may start at the mismatch. This process is discussed in further detail below.

Figure 2:
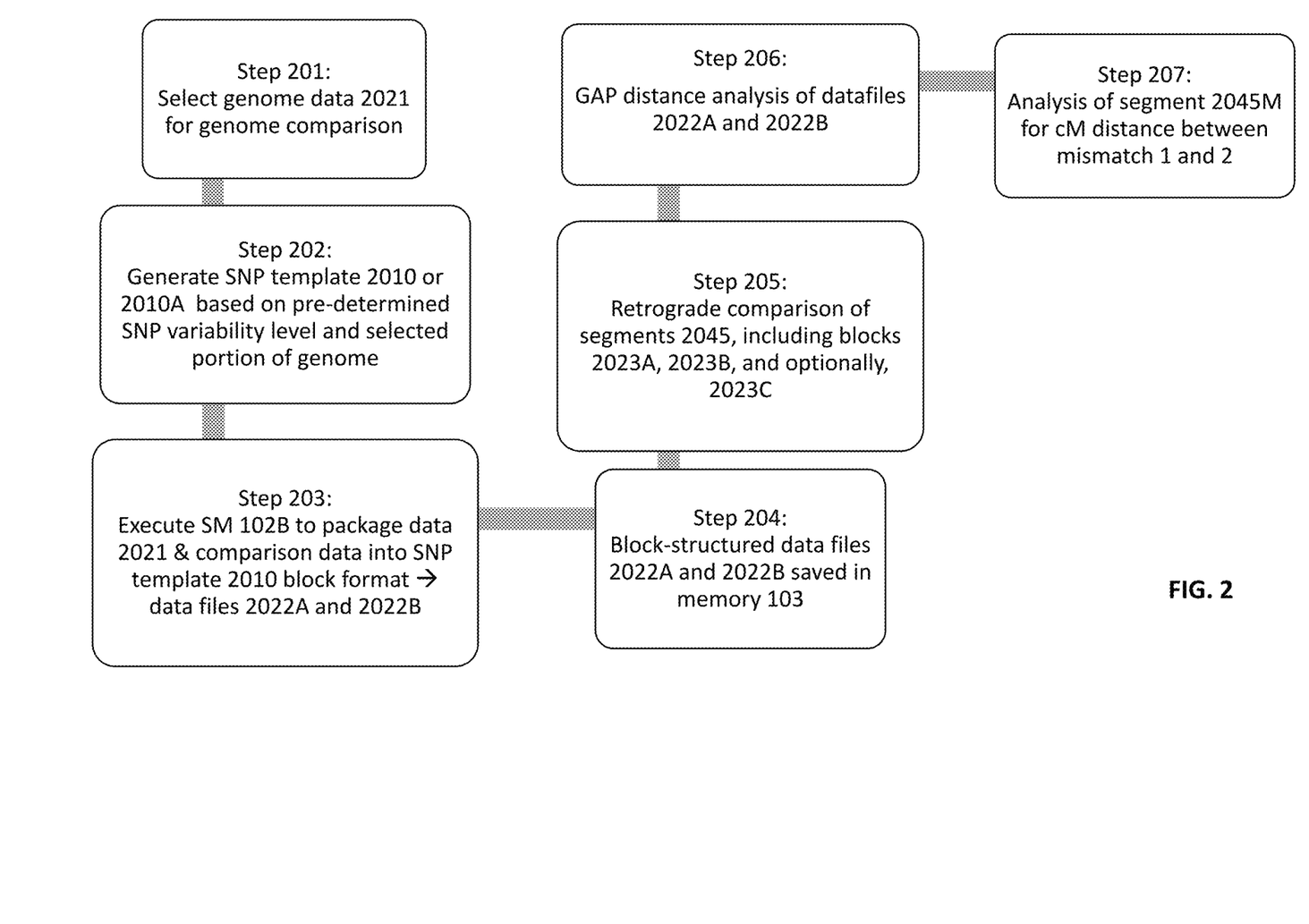
FIG. 2 shows a genome analysis method according to an embodiment of the present invention.
Figure 3:
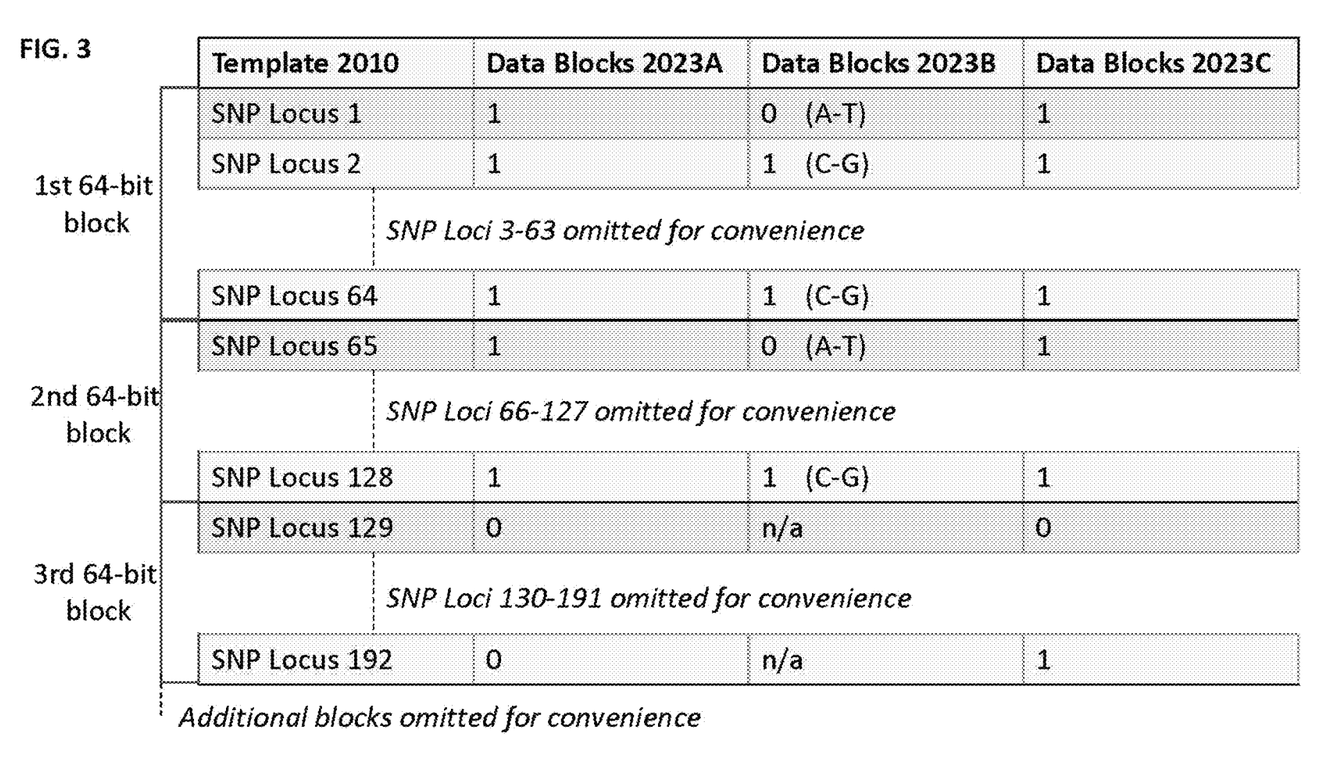
FIG. 3 shows genome data structuring according to an embodiment of the present invention.
Figure 4:
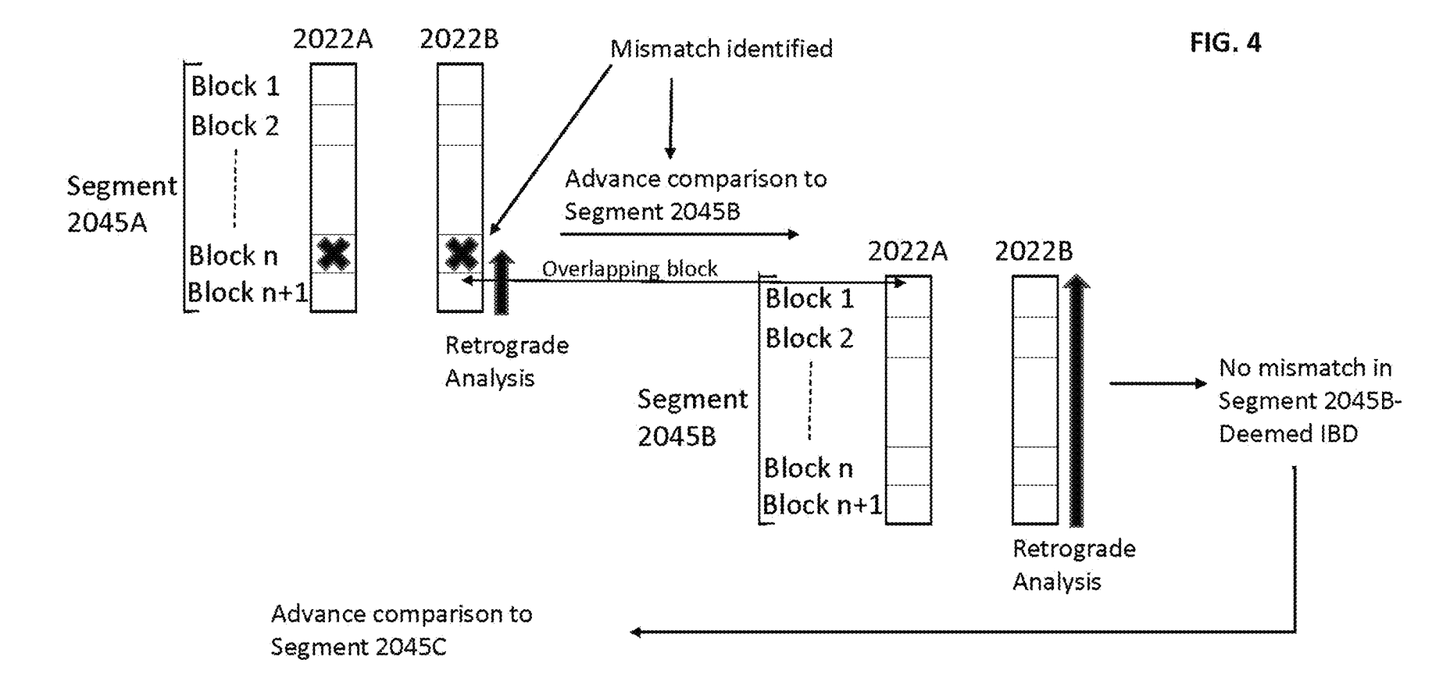
FIG. 4 shows a genome analysis method according to an embodiment of the present invention.

FIGS. 2-4 show a process flow 200 illustrating an embodiment of the present invention for processing genome data and compare the data to other genome data through a structured process. At step 201, genomic data may be selected for comparison from a DNA test sample or database records. At step 202, a comprehensive SNPs template 2010 may be generated that includes all known SNPs that have a pre-determined level of variability across individuals that they can be used to analyze two genomes for relatedness. In some implementations, SNPs that have a statistical variance of at least 5% may be included in the template 2010 (i.e., at least 5% of individuals in a sample population have a particular base pair—at least a 5:95 ratio). In other implementations, SNPs that have a statistical variance of at least 7.5%, at least 10%, or at least 15% to be included in the template 2010. The SNP template 2010 may be structured to allow organization of various DNA sequence data from individuals into a standardized format. In some embodiments, this template 2010 may include about 1.4 million SNPs in sequential genomic order (e.g., from human autosomal chromosome 1 to autosomal chromosome 22). In some embodiments, the number of SNPs in the template may be varied depending on the chromosomes selected for analysis. For example, certain chromosomes may be targeted for analysis: X chromosome may be included in the analysis, certain chromosomes may be excluded from the analysis, etc., resulting in a targeted SNP template 2010A that only includes a data structure for the targeted area of the genome.

The number and identity of SNPs in the SNPs template 2010 may be determined by (1) selecting the chromosomes to be analyzed, and (2) applying a frequency filter to known SNPs in the human genome to determine which SNPs vary often enough between individuals to warrant consideration in a half-matching analysis set at the preferred frequency of variance in the SNP markers (e.g., a pre-determined threshold of at least 5% variance, as discussed above). The applied frequency of variance between individuals may be selected based on the statistical reliability desired, the desired computing efficiency of DNA comparison analysis, and other criteria. Applying a reasonable threshold for frequency of variability for the SNPs yields about 1.4 million SNPs for analysis. The SNPs that are pre-selected for analysis are used to build the SNP template 2010, which will include a bit to identify each of those SNPs that qualify for analysis. The genome data 2021 from the sample to be compared and the comparison genome data 2022 from a second genome sequence (e.g., stored in database 103A) may both be organized according to the SNP template 2010. For situations in which the half-matching analysis is to be applied a targeted portion of the genome, the SNP template may be limited to the targeted portion of the genome, resulting a targeted SNP template 2010A.

At step 203, genome data 2021 for an individual provided from one or more data sets of genotyping data are received and converted into a data file according to the SNP template 2010. The data set 2021 may be from the DNA chip may be organized according to the SNPs template 2010. The SNPs template 2010 may include all SNPs that are analyzed by genealogical analysis vendors (e.g., 23andMe, ancentry.com, etc.). While the selection of SNPs varies from one vendor to the next based on the DNA chip technology they use and the particular criteria they apply, the predominant proportions of the SNPs analyzed by various vendors overlap and allow for comparison analysis of DNA kit data from various vendors using the SNP template 2010. The genome data 2021 (e.g., DNA genome data from a vendor's DNA kit) can be adapted to correspond to the SNPs template 2010 (or 2010A) so that comparison analysis with genomic data for another individual acquired from a different vendor that has also been organized into the SNPs template 2010 format can be compared without the need for sequence alignment analysis between the two genomes. All of the SNP data for genome data 2021 is prepackaged into a data file that matches the format of the SNP template 2010 by the processor(s) 102 performing machine executable instructions from software module 102B. The software module 102B allows the processor(s) 102 to identify specific loci in the genome data 2021 corresponding to the SNPs in the SNP template 2010. DNA kits typically utilize encoding and marking protocols to identify the specific loci of the sequenced genome or the sequenced portion of the genome. For example, DNA kit vendors may use a standard build37 system for identifying genes and loci in the sequenced DNA, which includes Reference SNP Cluster numbers (RSid), which identifies a location of an SNP on a particular chromosome. The configuration of this SNPs data from the genome data 2021 into the SNP template 2010 format through the application of the software module 102B pre-aligns the data into a standardized arrangement of the selected SNPs (e.g., the roughly 1.4 million known SNPs of sufficient variability) prior to comparison with SNP data from another individual's DNA kit or some other selected DNA sequence file.

The DNA kit data provided from a particular DNA chip may be analyzed to collect all locus data in the genome data 2021 that correspond to the loci in the SNPs template 2010, and converted into a block-structured SNP data file 2022 in blocks 2023 of pre-determined bit lengths that correspond to the word length of the processor(s) 102 of the system 100 (e.g., 32 bit, 64 bit, 128 bit, etc.). The number of bits in each block 2023 may be the same as the word length of the processor(s) 102 to allow the block to be analyzed in one computing operation to achieve greater processing efficiency. In some embodiments, the blocks 2023 each have 64 bits, such that they can be analyzed by current 64-bit processing systems. However, it should be noted that the methods described herein can be adapted to other word-length processing, such as 128 bit, etc. In some implementations, software module 102B may instruct processor(s) 102 to conduct a first locus screen operation of the data blocks 2023, which may include a digital analysis (e.g., an AND comparison) between the blocks 2023 and the SNPs template 2010 to determine which SNP loci are present in the genome data 2021, and limit the comparisons made between the blocks 2023 and the one or more comparison sequences (sequences in database 103A) to those loci identified in the first locus screen operation as present in the blocks 2023.

The SNPs template 2010 may include two or more sets of blocks 2023 that correspond to each position in the SNPs template 2010, with the first blocks 2023A indicating whether or not a particular SNP is homozygous and should be analyzed because it provides useful data for a half-matching analysis. Homozygous base pairs are needed to conduct the half-matching analysis. Each locus in the genome (including all SNP locations) have two base pairs (one on each of the corresponding chromosomes from individual's parents), each having one of two possible base pairs (A-T and C-G). If a person is heterozygous, both possible base pairs are present at that particular locus of the genome and there will be a half-match between the individual and the compared genome, regardless of the genotype of the compared genome, which provides no useful information. Thus, the SNPs compared between two genomes may be limited to SNP loci for which the particular individual has a homozygous genotype. The software module 102B may enable processor(s) 102 to create a first block 2023A that provides a token at each SNP location that corresponds to the SNPs template 2010. The token indicates whether the SNPs are appropriate for analysis (e.g., a "1" for the presence of homozygous base pairs at a SNP location, and a "0" value for no data or heterozygous base pairs).

The SNPs template 2010 may also include second blocks 2023B that may indicate the identity of the homozygous alleles at each selected SNP locus in the genome. The restriction of the analysis to only SNP loci where the base pairs are homozygous allows for a single bit analysis for matching between the two kits. The second blocks 2023B provide the single bit token that indicates which of the homozygous base pairs in the block-structured data file 2022, e.g., where one base pair (e.g., A-T) is represented by a "0" value and the other possible base pair (e.g., C-G) is represented by a "1". The organization of the genome data 2021 by processor(s) 102 using the software module 102B into block-structured data file 2022A having blocks 2023 allows for a simple machine analysis can be conducted between the compared blocks of the two kits to determine whether the kits match or mismatch at the loci analyzed in the compared blocks in one computing operation (e.g., an OR operation). For example, a bitwise OR operation may be performed by the processor(s) 102 to generate a result array for the genome data 2021 being compared to the comparison genome data set from a database or other kit organized according to the SNPs template 2010 into comparison data set 2022B. For example, the processor 102 may have 64-bit word length, and a 64-bit block from second blocks 2023B representing 64 SNP loci from the genome data 2021 is compared with a 64-bit block representing the same 64 SNP loci from the comparison data's string of second blocks through an single OR operation of the 64-bit processor 102. The OR operation may include OR analysis between each set of matching tokens (matching loci) in each of the 64-bit blocks: e.g., OR operation between the $1^{st}$ bit of the test kit block with the $1^{st}$ bit of the comparison kit block, OR operation between the $2^{nd}$ bit of the test kit block with the $2^{nd}$ bit of the comparison kit block, and so on). If no opposite-homozygous tokens between corresponding tokens (matching loci) in the compared blocks are present, all OR operation values will be zero, resulting in a total OR operation value of 0 for the compared blocks. In the case of no mismatches, the analysis continues to the next corresponding set of blocks. The first block 2023A analysis restricts the reporting of the second block 2023B analysis to only SNP loci where the genotype of the genome data 2021 is homozygous, thereby providing a filter on the second block analysis, identifying only the loci that are (1) relevant to the half-matching analysis and (2) reportable in the comparison analysis. This data arrangement and analysis greatly increases the computing efficiency of the presently disclosed system, and greatly reduces the time required for the half-matching analysis of the genomic data in the block-structured data file 2022.

In some embodiments, the SNP template 2010 and the block-structured data file 2022 may have a 3-bits per SNP position (the 3-bit embodiment). In such embodiments, the first block 2023A may indicate whether the SNP was analyzed by the DNA kit and is homozygous, the second block 2023B may provide the identity of the homozygous allele at the SNP locus, and a third set of blocks 2023C may provide a one-bit token to indicate whether a heterozygous SNP is present at the locus. Thus, the first two one-bit tokens at each SNP locus may be structured in the same manner as in the 2-bit implementation (as in blocks 2023A and 2023B), and a third bit for each SNP locus may provides additional information about whether an SNP was tested at a locus and was found to be heterozygous. The 3-bit version allows for exact reporting on the number of SNPs in a matching segment and the overlap of reported SNPs between two compared kits, rather than estimates of these numbers. The analysis of heterozygous matching allows for better analysis of kits from different DNA microarray chips with significant differences in the reported SNPs (referred to as "poor alignment"). If the number of overlapping SNPs is too small, the kits may not be reliably analyzed. The 3-bit analysis allows for examination of the heterozygous overlapping SNPs and thus an exact counting of the number of overlapping SNPs. With the analysis of the $3^{rd}$ bit, two kits may have a sufficient number of overlaps for reliable half-matching analysis.

The 3-bit version of the SNP template 2010 may also allow for analysis of the block-structured data file 2022 for a minimum SNP parameter for a "matching" segment. In addition to the minimum cM segment length requirement, the matching criteria may include a minimum number of SNPs parameter (e.g., a minimum of 400 SNPs) to qualify a matching segment as having a sufficient length to be statistically meaningful. The 3-bit version of the SNP template 2010 allows for accounting for both for reported homozygous and heterozygous SNPs in the segment, thus improving the reliability of the increasing the reported total SNPs and making it more likely that a segment having a sufficient number of SNPs is reported as such.

FIG. 3 provides a block diagram of the data file 2022 structure, where a 64-bit processor is used. The SNPs template 2010 defines block lengths of 64 bits and the data file 2022 is organized into block strings 2023A, 2023B, and optionally 2023C. Each of the blocks in each string is aligned with the other, with each bit position in the blocks in 2023A being alignment with the corresponding bit position in 2023B and 2023C. For convenience and presentation on one sheet, only three blocks are presented with the majority of the loci removed and represented with dashed lines, as noted in FIG. 3. It should be noted that typically only about one third of the loci in a DNA kit sequence are reported and homozygous.

In some embodiments, two or more data sets from two or more data sources (e.g., different genetic analysis services, databases, etc.) for an individual may be collated, aligned, and merged to create a single data set. For example, system 100 can receive the data sets from a genotyping lab through an electronic transfer (e.g., a Secure File Transfer Protocol-"SFTP"). The processor(s) 102 may process each data set using the software module 102A and stores the data machine readable media of memory 103. Each data set may be first organized into the structure of the SNPs template 2010. For example, the processor(s) 102 may receive two data sets for a single individual from one or more databases or genotyping labs, and may then restructure each data set according to the SNPs template 2010 to yield structured data sets 2032A and 2032B. The two data sets may be complete genomic data sets or partial data sets (e.g., one of the sequences may be a sequence of a limited number of chromosomes). In some embodiments, the processor(s) 102 may compare the data sets 2032A and 2032B to align and compare the datasets to merge the structured data from the two data sets to create a comprehensive data file 2032C. The merging process may also determine whether there is duplicate and/or conflicting data between the data sets 2032A and 2032B. Duplicate data in overlapping areas of the data sets 2032A and 2032B may be excluded from the comprehensive block-structured data file 2032C, resulting in a single set of merged data does not include duplicate SNP data organized into blocks according to the SNP template 2020.

At step 204, the block-structured data file 2022A (and 2022B, if it is not already saved in database 103A) for the individual may be recorded in a memory 103 of the server 101, allowing for the processor(s) 102 to access and analyze the datasets. The data sets 2032A, 2032B, and/or 2032C may also be stored in database 103A making the datasets available for later comparisons.

At step 205, the block-structured data file 2022A (or 2032C) may be compared to a reference data file 2022B, which may be data file containing the genomic data from a relative, genomic data from an unknown source, or other genomic data file that is also organized according to the SNP block template 2010 to yield a block-structured comparison data file 2022B. The block packaging of the DNA kit data into the block-structured data file 2022A allows for a novel approach for analyzing the base pair data that avoids having to sequentially analyze all of the SNPs loci in the genomic data. In some implementations, software module 102B may instruct processor(s) 102 to conduct a second locus screen operation of the data blocks 2023 for the structured data file 2022A and the structured comparison file 2022B, which may include a digital analysis (e.g., an AND comparison) between the blocks 2023 of 2022A and 2022B to determine which SNP loci are present both 2022A and 2022B, and limit the comparisons made between the blocks 2023 of structured data file 2022A and the structured comparison file 2022B to those loci identified in the second locus screen operation as present in structured data file 2022A and the structured comparison file 2022B. This screening process may further reduce the amount of comparisons made between structured data file 2022A and the structured comparison file 2022B and reduce the required computational load. The loci included in the blocks 2023 may be re-organized to remove those loci that do not have data for both the structured data file 2022A and the structured comparison file 2022B, reducing the total number of loci to be compared and potentially reducing the number of blocks 2023 in each data file 2022A and 2022B to be compared. The sequence alignment between 2022A and 2022B may be maintained, with the same loci being screened out of each datafile 2022A and 2022B.

The processor(s) 102 may include a software module 102C providing machine executable instructions to compare block-structured data files 2022A and 2022B (block sets 2023A and 2023B) within a segment of SNP loci of a pre-determined length in a retrograde manner that allows for many of the blocks in the genomic data file to be skipped over without sacrificing any useful information, thereby greatly reducing the computing load of the genomic comparison analysis. Executing the code of software module 102C, the processor(s) 102 first determines the required minimum cM length criteria of a minimum length DNA segment 2045 within the block-structured data files 2022A and 2022B to be analyzed. The predetermined length of a matching minimum DNA segment 2045 may have a statistically acceptable IBD match (e.g., 7 cM). Based on the required cM length criteria of a minimum segment 2045, the processor(s) 102 executes the instructions of software module 102C to precompute how many consecutive blocks 2023B need to be free of SNP mismatches with the comparison data file 2022B to satisfy the minimum cM length criteria. The processor(s) 102 may then find the last block 2023B in the minimum segment 2045 and begin comparing the blocks 2022B to the blocks of comparison data file 2022B in a first minimum segment 2045A in a retrograde direction—from the end of the segment 2045A toward the beginning of the segment 2045A. The retrograde analysis is more efficient than typical forward analysis because once a mismatch is found in the segment, every other block in the segment may be ignored and the processor(s) 102 advances the comparison analysis to a next segment 2045B having the minimum segment length according to the instructions of software module 102C. The next segment 2045B may begin at the first mismatch encountered in the retrograde analysis of the blocks in the segment 2045A and may end at a consecutive number of blocks that corresponds to the minimum cM length criteria. The processor 102 may then start the retrograde analysis process again at the last block in the second segment 2045B. The retrograde analysis process discussed above avoids wasted computing bandwidth and time that would otherwise be used in examining the remaining blocks in the segment 2045A. A graphical representation of this process is provided in FIG. 4.

In step 206, the software module 102B may further analyze overlapping SNPs to check for GAP distances between the compared sequences that result from sections of poor overlap between genomes or portions of genomes because they were sequenced by different DNA sequencing vendors using different chip sets and kits. A predetermined gap distance may be selected for analyzing the overlap of the compared sequences 2022A and 2022B. For example, a gap distance of about 3 cM may be selected. The GAP analysis locates gaps of 3 cM or more where there is poor overlap indicated by no aligned SNPs between the two data sets, and the edges or ends of such gaps are treated as mismatches in the sequence comparisons due to the statistical unreliability of poorly aligned sections of the genome. The GAP analysis may be carried out simultaneously with the retrograde analysis of the block-structured data in step 205.

In the event that a segment 2045M represented by a consecutive set of blocks satisfies the minimum cM length (i.e., it has been determined to have a number of consecutive blocks without mismatches that is at least as long as the minimum CM length and is ended by a block with at least one mismatch), it may be counted as an IBD match.

In step 207, the processor(s) 102 may further analyze a segment 2045M to determine the last mismatch position in the first block analyzed and the first mismatch position in last block analyzed according to the instructions of software module 102C. From there, a more precise calculation of the total length of the matching segment 2045M can be determined. This may be particularly important where the segment 2045M just meets the minimum CM length requirement. Because of the nature of the analysis of each word length block that is analyzed in one computing operation yielding a single bit output, there are situations where the length of segment 2045M is determined to be about equal to the minimum segment cM length based on the block analysis. Further analysis may be performed in order to determine that the segment 2045M actually meets the minimum cM length. The number of SNPs represented in each block with equal the word length of the processor(s) 102 (e.g., 32, 64, 128, etc.), and if a mismatch is found in a block, it may be near the beginning of the block or near the end of the block. After the mismatch ("mismatch 1") is found, the block analysis will proceed from the block containing the mismatch 1 to determine whether the segment 2045M beyond mismatch 1 has sufficient number of matching blocks to satisfy the minimum CM length. If the segment 2045M has a length that meets only the minimum number of blocks when a second mismatch ("mismatch 2") is found, it is indeterminate whether the segment actually meets the minimum CM length because mismatch 1 may be near the end of the first block and mismatch 2 may be near the beginning of the last block. This would render the segment 2045M between mismatch 1 and mismatch 2 slightly less than the minimum CM length. The exact length of the segment 2045M can be determined by the software module 102C, such as by determining the locus of the SNP mismatches 1 and 2 within the beginning and end blocks of the segment 2045M and calculating the distance between them. In other implementations, the minimum number of blocks of segment 2045 needed to meet the cM length may be adjusted to include one additional block to account for such eventualities.

As mentioned above, the system 100 may be used in process 200 to evaluate the overlapping homozygous SNPs (in the 2-bit version) or the total number of overlapping SNPs (in the 3-bit version) in the segment. These analyses can be done quickly because there are simple machine instructions to count the number of bits in a block that include a bit indicating the presence of a SNP in a block (e.g., a 1 for presence vs. a 0 for absence).

It should be understood that the foregoing descriptions of specific embodiments of the present invention have been presented for purposes of illustration and description. They are not intended to be exhaustive or to limit the invention to the precise forms disclosed, and obviously many modifications and variations are possible in light of the above teachings. The embodiments were chosen and described in order to best explain the principles of the invention and its practical application, and to thereby enable others skilled in the art to best utilize the invention and various embodiments with various modifications as are suited to the particular use contemplated.

What is claimed is:

1. A computer-implemented method for determining the genetic relatedness of multiple individuals of a particular species with fewer computational steps by a processor, comprising executing on a processor the steps of:

obtaining from a computer memory digital files of a first deoxyribonucleic acid (DNA) sequence information of a first individual and a second DNA sequence information of a second individual, each of said first and second DNA sequence information including base pair data for a set of single nucleotide polymorphism (SNP) loci;

said processor organizes the base pair data of each of said first and second DNA sequence information, wherein the base pair data present at each of said set of SNP loci are transformed into a standardized SNP data sequence format according to a digital SNP loci template having a pre-determined set of SNP loci, wherein a first digital file comprising a first standardized SNP sequence from said first DNA sequence and a second digital file comprising second standardized SNP sequence from said second DNA sequence are created, wherein each bit in said first standardized SNP sequence and said second standardized SNP sequence represents a base pair at one of said pre-determined set of SNP loci;

said processor divides the first standardized SNP sequence into a first set of digital data blocks and the second standardized SNP sequence into a second set of digital data blocks, each of said data blocks having a pre-determined bit length that is equal to a bit word length of said processor; and said processor compares said first set of digital blocks with said second set of digital blocks, wherein said first set of digital data blocks is aligned with said second set of digital data blocks according to said digital SNP loci template, a first predetermined sequence of digital data blocks of said first set of digital data blocks represents a first comparison segment and a first predetermined sequence of said second set of data blocks represents a second comparison segment, wherein the first comparison segment and said second comparison segment have a pre-determined segment length, and said processor performs the comparison of the first comparison segment and the second comparison segment in a stepwise block-by-block process beginning at a last digital data block of each of the first and second comparison segments, working backwards toward a first digital data block of each of the first and second comparison segments until
(1) a mismatch between the first and second comparison segments at an SNP locus is found or
(2) the entire lengths of the first and second comparison segments are compared with no mismatches at the SNP loci found,
wherein aligned digital data blocks are compared in a single computational step by the processor, and in the event a mismatch is identified in the comparison of the first comparison segment and said second comparison segment, a third comparison segment of said pre-determined segment length is identified starting from the last digital data block free from mismatches between the SNP loci of the first and second comparison segments and extending for said pre-determined segment length along said first set of digital data blocks, and a fourth comparison segment of said pre-determined segment length is identified starting from the last digital data block free from mismatches and extending for said pre-determined segment length along said second set of digital data blocks, and
said processor performing a comparison of the third comparison segment and the fourth comparison segment in a stepwise block-by-block process beginning at a last digital data block of each of the third and fourth comparison segments working backwards toward a first digital data block of each of the third and fourth comparison segments until
(1) a mismatch at an SNP locus between the third and fourth comparison segments is found or
(2) the entire lengths of the third and fourth comparison segments are compared with no mismatches at the SNP loci.

2. The method of claim 1, wherein said mismatch between base pairs of the first and second comparison segments occurs when they have opposite base pairs at a particular SNP locus.

3. The method of claim 1, wherein said first and second comparison segments include a pre-determined cM length requirement, defining said pre-determined segment length.

4. The method of claim 1, wherein each of the first and second DNA sequence information includes a single bit representing both sets of base pairs at each SNP locus in the digital SNP loci template for the corresponding individual.

5. The method of claim 4, further comprising creating a second bit corresponding to each SNP locus in the digital SNP loci template that encodes whether the sets of base pairs at said SNP locus are homozygous or heterozygous.

6. The method of claim 1, further converting a predetermined cM length requirement into a corresponding number of data blocks representing a number of SNP loci to satisfy the said predetermined cM length requirement, wherein said first comparison segment, said second comparison segment, said third comparison segment, and said fourth comparison segment each have a length that is equal to said predetermined cM length requirement.

7. A computer-implemented method for determining the genetic relatedness of multiple individuals executing machine-readable instructions on a general purpose computer, comprising:

obtaining first digital deoxyribonucleic acid (DNA) sequence data set of a first individual and second digital DNA sequence data set of a second individual from a computer memory;
a processor of said general purpose computer transforms base pair data at single nucleotide polymorphism (SNP) loci in the first digital DNA sequence data set to generate a first digital file comprising a first digital comparison sequence according to an SNP loci sequence template, wherein each bit in said first digital comparison sequence represents a homozygous set of base pairs at one of said SNP loci;
said processor transforms base pair data at SNP loci data in the second digital DNA sequence data to generate a second digital file comprising a second digital comparison sequence according to said SNP loci sequence template, wherein each bit in said second digital comparison sequence represents a homozygous set of base pairs at one of said SNP loci;
said processor divides the first comparison sequence into a first set of digital data blocks and the second comparison sequence into a second set of digital data blocks, wherein the number of bits in each digital data block is equal to the bit word length of a computer processor and each bit in each digital data block represents an identity of a set of homozygous base pairs at an SNP locus in the SNP loci sequence template; comparing a first set of digital data blocks from said first comparison sequence with a second set of digital data blocks from said second comparison sequence to identify mismatches in base pair data at SNP loci, wherein said first set of digital data blocks and said second digital data blocks are aligned according to said SNP loci sequence template and have a predetermined length that has a number of SNP loci required to satisfy a pre-determined centimorgan (cM) length, wherein said comparison begins between a last data block of said first set of digital data blocks and a last data block of said second set of digital data blocks and proceeds in a retrograde progression from the last data digital blocks until either a mismatch occurs between the first and second sets of digital data blocks at an SNP locus or the comparison does not identify a mismatch at any SNP locus; and
said processor determines whether the SNP loci of the first and second sets of digital data blocks match by comparing the bits between two corresponding digital data blocks of said first and second sets of digital data blocks in a single computational operation.

8. A digital computing system having a processor and, a computer-readable memory, and having software enabling said digital computing system to convert and compare digital DNA sequence data set from multiple individuals to determine the genetic relatedness of the multiple individuals with fewer computational operations by said processor, comprising:
said processor operable to:
obtain from a computer-readable medium first and second digital deoxyribonucleic acid (DNA) sequence data sets of a first individual and a second individual, respectively, said first and second digital DNA sequence data sets including base pair data for single nucleotide polymorphism (SNP) loci of said first and second individuals;
create first and second digital comparison sequences each comprising said base pair data at said SNP loci from said first and second digital DNA sequence data sets according to a digital SNP sequence template, wherein each bit in the first and second comparison sequences represents an identity of a base pair at an SNP locus;

divide the first comparison sequence into a first set of digital data blocks and the second comparison sequence into a second set of digital data blocks, each of said data blocks having a pre-determined bit length equal to a bit word length of said processor; and compare said first comparison sequence of said first individual with said second comparison sequence of said second individual in a stepwise block-by-block process beginning at a last digital data block of each of the first and second sets of digital data blocks and working backwards toward a first digital data block of each of the first and second sets of digital data blocks, wherein a. a comparison of one digital data block of said first set of digital data blocks and one digital block of said second set of digital data blocks is completed in a single computational operation by the processor, and b. said first set of digital data blocks is aligned with said second set of digital data blocks according to said digital SNP sequence template, such that bit values at the SNP loci in the one digital data block of said first set of digital data blocks and the one digital data block of said second set of digital data blocks are directly compared during said single computational operation.

9. The method of claim 1, said digital file of a first DNA sequence information is obtained from a first DNA kit and said second DNA sequence information is from a second DNA kit, wherein said first DNA kit and second DNA kit have partially differing sets of SNP loci, and said first DNA sequence information and said second DNA sequence information are organized according to said SNP loci template to pre-align the data to allow the first DNA sequence information and said second DNA sequence information to be compared for matching segments.

10. The method of claim 7, said first digital DNA sequence data set is obtained from a first DNA kit and said second digital DNA sequence data set is from a second DNA kit, wherein said first DNA kit and second DNA kit have partially differing sets of SNP loci, and said first digital DNA sequence data set and said second digital DNA sequence data set are organized according to said SNP sequence template to pre-align the data to allow the first DNA sequence information and said second DNA sequence information to be compared for matching segments.

11. The method of claim 8, said first digital DNA sequence data set is obtained from a first DNA kit and said second digital DNA sequence data set is from a second DNA kit, wherein said first DNA kit and second DNA kit have partially differing sets of SNP loci, and said first digital DNA sequence data set and said second digital DNA sequence data set are organized according to said digital SNP sequence template to pre-align the data to allow the first DNA sequence information and said second DNA sequence information to be compared for matching segments.

* * * * *